United States Patent
Rudser

(10) Patent No.: US 10,413,649 B2
(45) Date of Patent: Sep. 17, 2019

(54) BACK UP CONTROLLER SYSTEM WITH UPDATING

(71) Applicant: HeartWare, Inc., Miami Lakes, FL (US)

(72) Inventor: John Rudser, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 104 days.

(21) Appl. No.: 14/862,586

(22) Filed: Sep. 23, 2015

(65) Prior Publication Data

US 2016/0095968 A1 Apr. 7, 2016

Related U.S. Application Data

(60) Provisional application No. 62/058,165, filed on Oct. 1, 2014.

(51) Int. Cl.
  *G06F 1/32* (2019.01)
  *A61M 1/10* (2006.01)
  *A61M 1/12* (2006.01)

(52) U.S. Cl.
  CPC .......... *A61M 1/1086* (2013.01); *A61M 1/101* (2013.01); *A61M 1/122* (2014.02); *A61M 1/127* (2013.01);
  (Continued)

(58) Field of Classification Search
  CPC ............ A61M 1/1086; A61M 2205/33; A61M 2205/52; A61M 2230/005;
  (Continued)

(56) References Cited

U.S. PATENT DOCUMENTS

| 4,376,312 A | 3/1983 | Robinson et al. |
| 4,665,896 A | 5/1987 | LaForge et al. |

(Continued)

FOREIGN PATENT DOCUMENTS

| JP | 1993060112 | 8/1993 |
| JP | H1043291 A | 2/1998 |

(Continued)

OTHER PUBLICATIONS

WO99/32031, Peterson et al, Automatic Configuraion of Medical Equipment, Dec. 22, 19978.*

(Continued)

*Primary Examiner* — Zahid Choudhury
(74) *Attorney, Agent, or Firm* — Christopher & Weisberg, P.A.

(57) ABSTRACT

A medical device system includes a medical device configured to be carried by a patient and a plurality of controllers capable of controlling operation of the medical device. Each controller has an active state in which the controller is in communication with, and controls the operation of, the medical device, and a passive state in which the controller is not controlling operation of the medical device. At any given time only one of the plurality of controllers will be in the active state and a remainder of the plurality of controllers will be in the passive state. The active controller may be configured to continually communicate with the remainder of passive controllers, without using the medical device as an intermediary, to update the information stored in the memories of the passive controllers to match the information in the memory of the active controller.

22 Claims, 4 Drawing Sheets

(52) U.S. Cl.
CPC ..... *A61M 2205/33* (2013.01); *A61M 2205/52* (2013.01); *A61M 2230/005* (2013.01); *A61M 2230/06* (2013.01); *A61M 2230/207* (2013.01); *A61M 2230/50* (2013.01)

(58) Field of Classification Search
CPC ........ A61M 2230/06; A61M 2230/207; A61M 2230/50; G06F 1/3202; G06F 1/3231; G06F 1/26; G06F 1/206; G06F 1/3228; G06F 1/08; G06F 1/3289; G06F 1/266; G06F 1/02; H04L 12/12
See application file for complete search history.

(56) References Cited

U.S. PATENT DOCUMENTS

| | | |
|---|---|---|
| 4,666,443 A | 5/1987 | Portner |
| 5,569,156 A | 10/1996 | Mussivand |
| 5,704,891 A | 1/1998 | Mussivand |
| 5,810,758 A | 9/1998 | Yamazaki et al. |
| 6,123,726 A | 9/2000 | Mori et al. |
| 6,132,363 A | 10/2000 | Freed et al. |
| 6,183,412 B1 | 2/2001 | Benkowski et al. |
| 6,398,506 B1 | 6/2002 | Maekawa et al. |
| 6,547,530 B2 | 4/2003 | Ozaki et al. |
| 6,605,032 B2 | 8/2003 | Benkowski et al. |
| 6,652,447 B2 | 11/2003 | Benkowski et al. |
| 6,783,328 B2 | 8/2004 | Lucke et al. |
| 6,866,625 B1 | 3/2005 | Ayre et al. |
| 6,991,595 B2 | 1/2006 | Burke et al. |
| 7,033,147 B2 | 4/2006 | Yanai et al. |
| 7,150,711 B2 | 12/2006 | Nusser et al. |
| 7,160,242 B2 | 1/2007 | Yanai |
| 7,160,243 B2 | 1/2007 | Medvedev |
| 7,175,588 B2 | 2/2007 | Morello |
| 7,396,327 B2 | 7/2008 | Morello |
| 7,497,116 B2 | 3/2009 | Miyakoshi et al. |
| 7,563,225 B2 | 7/2009 | Sugiura |
| 7,794,384 B2 | 9/2010 | Sugiura et al. |
| 7,819,916 B2 | 10/2010 | Yaegashi |
| 7,824,358 B2 | 11/2010 | Cotter et al. |
| 7,859,208 B2 | 12/2010 | Ayre et al. |
| 7,861,582 B2 | 1/2011 | Miyakoshi et al. |
| 7,951,062 B2 | 5/2011 | Morello |
| 7,963,905 B2 | 6/2011 | Salmonsen et al. |
| 7,988,728 B2 | 8/2011 | Ayre |
| 8,096,935 B2 | 1/2012 | Sutton et al. |
| 8,157,721 B2 | 4/2012 | Sugiura |
| 8,206,278 B2 | 6/2012 | De Plater et al. |
| 8,210,829 B2 | 7/2012 | Horvath et al. |
| 8,221,303 B2 | 7/2012 | Ovil et al. |
| 8,226,373 B2 | 7/2012 | Yaegashi |
| 8,226,541 B2 | 7/2012 | Kantrowitz |
| 8,226,542 B2 | 7/2012 | Yaegashi |
| 8,226,543 B2 | 7/2012 | Tan et al. |
| 8,226,591 B2 | 7/2012 | Mazur |
| 8,226,712 B1 | 7/2012 | Frazier et al. |
| 8,229,543 B2 | 7/2012 | Zeijlemaker |
| 8,231,517 B2 | 7/2012 | Royalty |
| 8,231,518 B2 | 7/2012 | Royalty |
| 8,231,519 B2 | 7/2012 | Reichenbach et al. |
| 8,235,884 B2 | 8/2012 | Royalty et al. |
| 8,235,885 B2 | 8/2012 | Whisenant et al. |
| 8,235,933 B2 | 8/2012 | Keren et al. |
| 8,241,197 B2 | 8/2012 | Royalty |
| 8,241,198 B2 | 8/2012 | Bull et al. |
| 8,241,199 B2 | 8/2012 | Maschke |
| 8,246,530 B2 | 8/2012 | Sullivan |
| 8,246,671 B2 | 8/2012 | Khairkhahan |
| 8,255,050 B2 | 8/2012 | Mohl |
| 8,257,428 B2 | 9/2012 | Khairkhahan et al. |
| 8,262,580 B2 | 9/2012 | Mohl et al. |
| 8,266,943 B2 | 9/2012 | Miyakoshi et al. |
| 8,282,359 B2 | 10/2012 | Ayre et al. |
| 8,303,481 B2 | 11/2012 | Kassab et al. |
| 8,303,482 B2 | 11/2012 | Schima et al. |
| 8,323,173 B2 | 12/2012 | Benkowski et al. |
| 8,323,174 B2 | 12/2012 | Jeevanandam et al. |
| 8,328,751 B2 | 12/2012 | Keren et al. |
| 8,329,314 B1 | 12/2012 | Xiaohai et al. |
| 8,333,686 B2 | 12/2012 | Marseille et al. |
| 8,333,687 B2 | 12/2012 | Farnan et al. |
| 8,333,727 B2 | 12/2012 | Farnan |
| 8,343,028 B2 | 1/2013 | Gregoric et al. |
| 8,343,029 B2 | 1/2013 | Farnan et al. |
| 8,343,212 B2 | 1/2013 | Pickett et al. |
| 8,353,813 B2 | 1/2013 | Shaknovich |
| 8,366,411 B2 | 2/2013 | Baykut et al. |
| 8,366,599 B2 | 2/2013 | Tansley et al. |
| 8,371,997 B2 | 2/2013 | Shifflette |
| 8,376,926 B2 | 2/2013 | Benkowsi et al. |
| 8,376,927 B2 | 2/2013 | Tovar Lopez |
| 8,377,114 B2 | 2/2013 | Khairkhahan et al. |
| 8,382,651 B2 | 2/2013 | Kassab et al. |
| 8,382,653 B2 | 2/2013 | Dubi et al. |
| 8,382,695 B1 | 2/2013 | Patel |
| 8,382,830 B2 | 2/2013 | Maher et al. |
| 8,388,511 B2 | 3/2013 | Spence |
| 8,388,565 B2 | 3/2013 | Shifflette |
| 8,388,643 B2 | 3/2013 | Murayama et al. |
| 8,388,649 B2 | 3/2013 | Woodard et al. |
| 8,388,672 B2 | 3/2013 | Khairkhahan et al. |
| 8,394,008 B2 | 3/2013 | Annest et al. |
| 8,394,009 B2 | 3/2013 | Bolyard et al. |
| 8,394,010 B2 | 3/2013 | Farnan |
| 8,396,566 B2 | 3/2013 | Kassab et al. |
| 8,398,536 B2 | 3/2013 | Vodermayer et al. |
| 8,398,537 B2 | 3/2013 | Khairkhahan et al. |
| 8,449,444 B2 | 5/2013 | Poirier |
| 8,506,471 B2 | 8/2013 | Bourque |
| 8,545,381 B2 | 10/2013 | Kanebako |
| 8,556,795 B2 | 10/2013 | Bolyard et al. |
| 8,562,507 B2 | 10/2013 | Poirier |
| 8,562,508 B2 | 10/2013 | Dague et al. |
| 8,585,571 B2 | 11/2013 | Bachman et al. |
| 8,613,696 B2 | 12/2013 | Medvedev et al. |
| 8,631,680 B2 | 1/2014 | Fleischli et al. |
| 8,636,638 B2 | 1/2014 | Timms |
| 8,652,024 B1 | 2/2014 | Yanai et al. |
| 8,657,733 B2 | 2/2014 | Ayre et al. |
| 8,672,868 B2 | 3/2014 | Simons |
| 8,682,431 B2 | 3/2014 | Callaway et al. |
| 8,715,151 B2 | 5/2014 | Poirier |
| 8,721,719 B2 | 5/2014 | Burke |
| 8,727,960 B2 | 5/2014 | Kanebako |
| 8,747,293 B2 | 6/2014 | Arndt et al. |
| 8,753,256 B2 | 6/2014 | Bolyard et al. |
| 8,794,989 B2 | 8/2014 | Kearsley et al. |
| 8,827,888 B2 | 9/2014 | Bolyard et al. |
| 8,827,890 B2 | 9/2014 | Lee et al. |
| 8,834,345 B2 | 9/2014 | Yanai et al. |
| 8,837,096 B2 | 9/2014 | Seebruch |
| 8,858,416 B2 | 10/2014 | Crosby et al. |
| 8,870,552 B2 | 10/2014 | Ayre et al. |
| 8,876,685 B2 | 11/2014 | Crosby et al. |
| 8,905,910 B2 | 12/2014 | Reichenbach et al. |
| 8,932,197 B2 | 1/2015 | Gregoric et al. |
| 8,939,883 B2 | 1/2015 | Callaway et al. |
| 8,956,275 B2 | 2/2015 | Bolyard et al. |
| 8,961,388 B2 | 2/2015 | Bourque |
| 8,968,174 B2 | 3/2015 | Yanai et al. |
| 9,011,312 B2 | 4/2015 | Bourque |
| 9,039,595 B2 | 5/2015 | Ayre et al. |
| 9,056,159 B2 | 6/2015 | Medvedev et al. |
| 2003/0069465 A1 | 4/2003 | Benkowski et al. |
| 2004/0097782 A1 | 5/2004 | Korakianitis et al. |
| 2007/0072549 A1* | 3/2007 | Carolan ................ H04B 15/02 455/63.1 |
| 2007/0142696 A1* | 6/2007 | Crosby ................ A61M 1/101 600/16 |
| 2007/0173898 A1* | 7/2007 | Ayre ....................... A61N 1/37 607/33 |
| 2007/0174686 A1* | 7/2007 | Douglas ............. G06F 11/2097 714/13 |

(56) References Cited

U.S. PATENT DOCUMENTS

| | | |
|---|---|---|
| 2007/0197854 A1 | 8/2007 | Marseille et al. |
| 2008/0147962 A1* | 6/2008 | Diggs .............. G06F 11/1456 711/103 |
| 2010/0094221 A1 | 4/2010 | Spencer et al. |
| 2011/0071336 A1* | 3/2011 | Yomtov .............. A61M 1/127 600/16 |
| 2012/0022645 A1* | 1/2012 | Burke .............. A61M 1/1086 623/3.13 |
| 2012/0142994 A1 | 6/2012 | Toellner |
| 2012/0142995 A1 | 6/2012 | Tao et al. |
| 2012/0142996 A1 | 6/2012 | Criscione |
| 2012/0142997 A1 | 6/2012 | Duenas |
| 2012/0142998 A1 | 6/2012 | Ogawa et al. |
| 2012/0149970 A1 | 6/2012 | Jeevanandam et al. |
| 2012/0149971 A1 | 6/2012 | Jeevanandam et al. |
| 2012/0150291 A1 | 6/2012 | Aber et al. |
| 2012/0157753 A1 | 6/2012 | D'Ambrosio |
| 2012/0157754 A1 | 6/2012 | D'Ambrosio |
| 2012/0157755 A1 | 6/2012 | D'Ambrosio |
| 2012/0157756 A1 | 6/2012 | Min et al. |
| 2012/0165931 A1 | 6/2012 | Bourque |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0172657 A1 | 7/2012 | Marseille et al. |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0190913 A1 | 7/2012 | Mohl |
| 2012/0203056 A1 | 8/2012 | Corbett |
| 2012/0209057 A1 | 8/2012 | Siess et al. |
| 2012/0220815 A1 | 8/2012 | Richardson et al. |
| 2012/0226096 A1 | 9/2012 | Callaway et al. |
| 2012/0226097 A1 | 9/2012 | Smith et al. |
| 2012/0226350 A1 | 9/2012 | Rudser et al. |
| 2012/0232331 A1 | 9/2012 | Nour |
| 2012/0245404 A1 | 9/2012 | Smith et al. |
| 2012/0245405 A1 | 9/2012 | Tatum et al. |
| 2012/0253103 A1 | 10/2012 | Robert |
| 2012/0259157 A9 | 10/2012 | Spence |
| 2012/0265002 A1 | 10/2012 | Roehn et al. |
| 2012/0265003 A1 | 10/2012 | D'Ambrosio et al. |
| 2012/0271096 A1 | 10/2012 | Gelbart et al. |
| 2012/0277520 A1 | 11/2012 | Duncan |
| 2012/0283506 A1 | 11/2012 | Meister et al. |
| 2012/0296151 A1 | 11/2012 | Curtis et al. |
| 2012/0296152 A1 | 11/2012 | Reichenbach et al. |
| 2012/0296153 A1 | 11/2012 | Laufer et al. |
| 2012/0310036 A1 | 12/2012 | Peters et al. |
| 2012/0310037 A1 | 12/2012 | Choi et al. |
| 2012/0316383 A1 | 12/2012 | Mohl |
| 2012/0323065 A1 | 12/2012 | Mohl et al. |
| 2013/0006041 A1 | 1/2013 | Schweich, Jr. et al. |
| 2013/0012761 A1 | 1/2013 | Gregoric et al. |
| 2013/0023721 A1 | 1/2013 | Matheny |
| 2013/0030240 A1 | 1/2013 | Schima et al. |
| 2013/0030522 A1 | 1/2013 | Rowe et al. |
| 2013/0041202 A1 | 2/2013 | Toellner |
| 2013/0041203 A1 | 2/2013 | Heilman et al. |
| 2013/0041204 A1 | 2/2013 | Heilman et al. |
| 2013/0041460 A1 | 2/2013 | Heilman et al. |
| 2013/0046129 A1 | 2/2013 | Medvedev et al. |
| 2013/0046130 A1 | 2/2013 | Hastie et al. |
| 2013/0053622 A1 | 2/2013 | Corbett |
| 2013/0053623 A1 | 2/2013 | Evans et al. |
| 2013/0053624 A1 | 2/2013 | Zilbershlag |
| 2013/0053625 A1 | 2/2013 | Merce Vives |
| 2013/0060077 A1 | 3/2013 | Liebing |
| 2013/0066139 A1 | 3/2013 | Wiessler et al. |
| 2013/0066140 A1 | 3/2013 | McBride et al. |
| 2013/0066141 A1 | 3/2013 | Doerr et al. |
| 2013/0066142 A1 | 3/2013 | Doerr et al. |
| 2014/0039455 A1 | 2/2014 | Miller et al. |
| 2014/0243970 A1* | 8/2014 | Yanai .............. A61M 1/1086 623/3.28 |
| 2015/0095696 A1* | 4/2015 | Hess .............. G06F 11/108 714/6.24 |
| 2015/0238717 A1* | 8/2015 | Hatanaka .......... A61M 1/1086 700/90 |

FOREIGN PATENT DOCUMENTS

| | | |
|---|---|---|
| JP | H10-085322 A | 4/1998 |
| JP | H10-127758 A | 5/1998 |
| JP | 2002-505919 A | 2/2002 |
| JP | 2005-236085 A | 9/2005 |
| JP | 2006-514842 A | 5/2006 |
| WO | 99/45981 A1 | 9/1999 |
| WO | 00/59560 A1 | 10/2000 |
| WO | 2004017831 A1 | 3/2004 |
| WO | 2007053881 A1 | 5/2007 |
| WO | 2011005633 A2 | 1/2011 |
| WO | 2011035308 A1 | 3/2011 |

OTHER PUBLICATIONS

International Search Report for Application No. PCT/US2015/051475 dated Dec. 23, 2015.

El-Banayosy, et al., "The European Experience of Novacor Left Ventricular Assist (LVAS) Therapy as a Bridge to Transplant: A Retrospective Multi-Centre Study" Eur. J. Cardio-Thoracic Surgery: vol. 15, pp. 835-841 (1999).

Extended European Search Report dated Jan. 22, 2014, in EP Patent Application No. 08770343.5.

China National Intellectual Property Administration, Notice on the First Office Action and Search Report, dated Mar. 5, 2019 for corresponding International Application No. 201580065149.0.

* cited by examiner

BACK UP CONTROLLER SYSTEM WITH UPDATING

CROSS-REFERENCE TO RELATED APPLICATIONS

The present application claims the benefit of the filing date of U.S. Provisional Application No. 62/058,165, filed Oct. 1, 2014, entitled BACKUP CONTROLLER SYSTEM WITH UPDATING, the disclosure of which is hereby incorporated herein by reference.

BACKGROUND

Medical device systems are being developed for long-term treatment of chronic conditions. Because of the nature of chronic conditions, patients may need to carry a medical device on their person regularly. For example, ventricular assist devices ("VADs") to treat chronic heart failure may be fully implantable and thus carried by the patient at all times. Similarly, drug pumps may be carried on a patient, either fully implanted or with transcutaneous components, to provide medicine as necessary to treat a condition. These include, for example, fully or partially implantable insulin pumps that deliver insulin from a medicinal reservoir in the device to the body to the patient to manage diabetes.

These types of medical devices often have controllers that store information and provide some level of automation to the medical device. For example, in addition to a VAD, a medical device system may include a handheld controller outside the body connected to the VAD via a wired connection, such as a transcutaneous electrical cable, or via a wireless connection. The controller may provide operating instructions to the VAD and store information relating to current and past operation of the VAD as well as physiological data sensed by the VAD. Other medical devices may work similarly. For example, insulin pumps may include a controller portion separate from an insulin containing and pumping mechanism. In both cases, patients may have one or more backup or secondary controllers so that, in the event of failure of a primary or active controller, the patient may disconnect the failed controller and replace it with a backup controller to provide continuity of treatment.

Although there may be varying levels of criticality to continuity of treatment, in most cases it is desirable to have the medical device return to full functionality as soon as possible following failure of the controller. In the case of a VAD, this may be highly critical. If a VAD controller suffers catastrophic failure, operating instructions and/or power to the VAD may be interrupted, in turn interrupting sufficient blood flow to the patient. For insulin pumps, perhaps potentially less critical, a failed controller may limit or completely hinder the patient from receiving any basal and/or bolus deliveries of insulin, potentially putting the patient at serious risk of a hypoglycemic event.

As medical device technology develops, controllers of medical devices may provide more complex and effective control of the medical device. Further, the controllers may store a broad range of information, such as device and patient health information. As the patient's experience with use of the medical device grows, controllers may be updated to deliver more optimal control and may acquire more data relating to operation of the medical device system and/or parameters of the patient, such as pressures experienced in the heart or glucose levels existing in the blood.

If a medical device controller is updated, for example by a clinician to provide different operating instructions, or by the accumulation of historical data, those updates are generally stored only within the controller connected to the medical device. If failure of the controller does occur and a backup controller is connected to the medical device in place of the failed controller, the newly connected controller will not have all of the same information stored in its memory. Thus, important information may be lost and the operation of the medical device under the control of the newly connected controller may be different than the operation of the medical device under the previous controller before it failed or was switched out for a secondary controller.

BRIEF SUMMARY

In one embodiment of the disclosure, a medical device system includes a medical device configured to be carried by a patient and a plurality of controllers capable of controlling operation of the medical device. Each controller may have an active state in which the controller is in communication with the medical device and is controlling operation of the medical device, and a passive state in which the controller is not controlling operation of the medical device. Each controller may also have a memory for storing information. The medical device and controllers may be constructed and arranged so that at any given time only one of the plurality of controllers will be in the active state and a remainder of the plurality of controllers will be in the passive state. The controller in the active state may be configured to continually communicate with the remainder of controllers in the passive state, without using the medical device as an intermediary, to update the information stored in the memories of the remainder of controllers in the passive state to match or provide a redundant copy of the information in the memory of the controller in the active state.

According to another embodiment of the disclosure, a method of operating a medical device system includes controlling a medical device carried by a patient with one of a plurality of controllers. The one of the plurality of controllers is in an active state in which the controller is in communication with the medical device and is controlling operation of the medical device, while a remainder of the plurality of controllers are in a passive state in which the controller is not controlling operation of the medical device. The controller in the active state may communicate with the remainder of the plurality of controllers in the passive state, without using the medical device as an intermediary, to continually update information stored in a memory of each controller in the passive state to match information stored in a memory of the controller in the active state.

DETAILED DESCRIPTION

Figure 1:
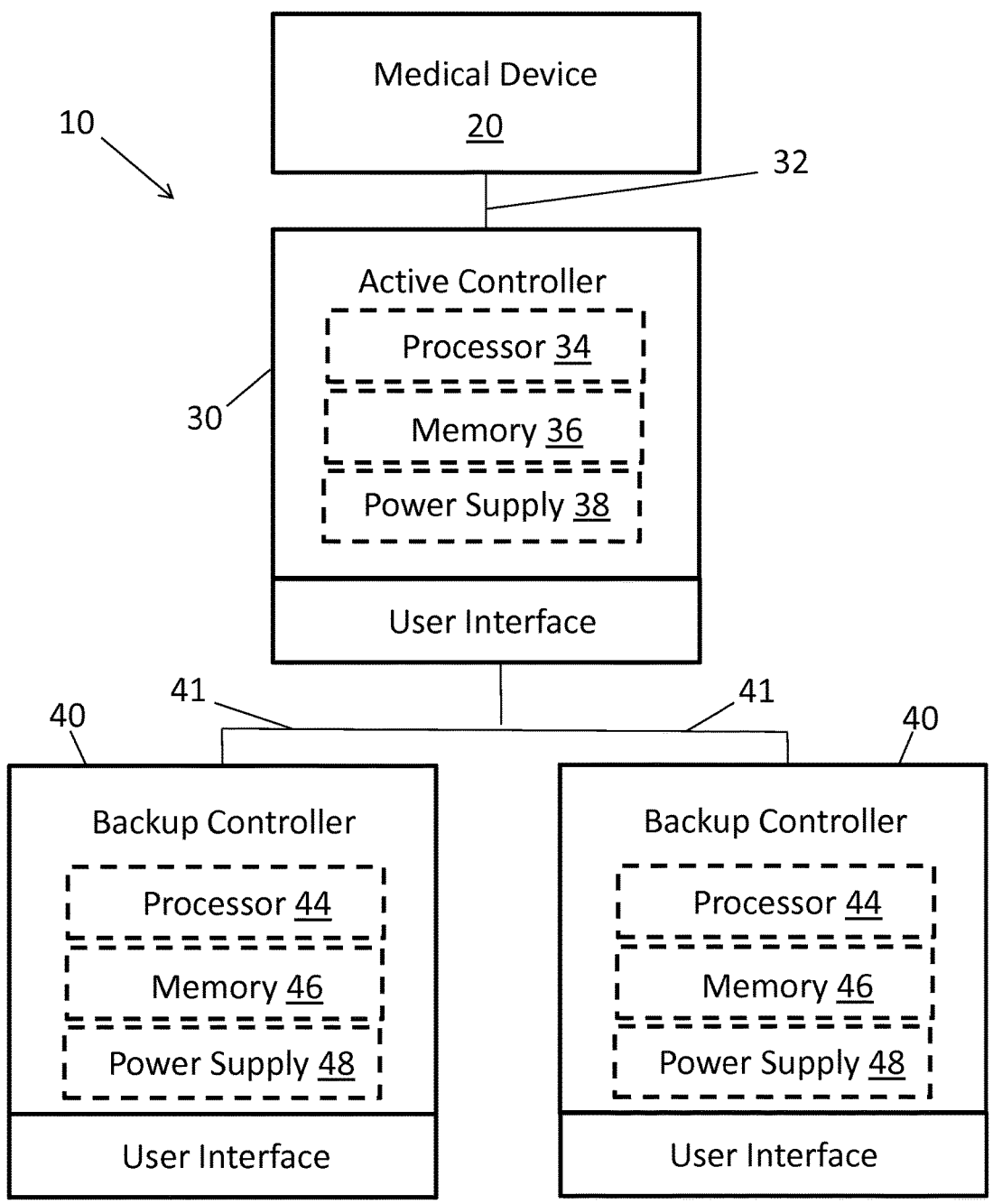
FIG. 1 is a diagrammatic view of medical device system according to an aspect of the disclosure.

FIG. 1 is a diagrammatic view of a medical device system 10. Medical device system 10 may generally include a medical device 20, a controller 30 for controlling medical device 30, and one or more backup or secondary controllers 40.

Medical device 20 may be configured to be carried on a patient, for example via full or partial implantation, or by being externally worn or held by the patient. Medical device 20 may be, for example, a VAD or other heart assisting device or an infusion device, such as a partially or fully implantable insulin pump or artificial pancreas.

Controller 30 may take any suitable form, including, for example, a handheld device or a device configured to couple to medical device 20 to form a single unit. Medical device 20 and controller 30 may be connected via a pathway 32. Pathway 32 may be a physical connection, such as an electrical cable to provide information and/or power to operate medical device 20, or may be a wireless connection. Controller 30 may also include a processor 34 for processing information, a memory 36 for storing information, and a power supply 38 for powering the controller 30 and/or medical device 20. As shown in the figure, controller 30 may also include a user interface, which may be physically part of controller 30, such as a touch screen and/or buttons, or may be a separate interface device coupled to controller 30. It should be understood that one or more external power supplies may be connected to controller 30 in addition or alternative to internal power supply 38. For example, one or more external battery packs and/or leads connected to AC power may provide power for controller 30 and/or medical device 20.

Controller 30 may have an active state in which the controller 30 is in communication with, or is in primary command and control of, the medical device 20 via pathway 32 and is controlling operation of the medical device 20. Controller 30 may also have a passive state in which the controller 30 is not controlling operation of the medical device 20. As illustrated, controller 30 is in the active state. While in the active state, controller 30 may control medical device 20 by, for example, providing a speed at which a pump is set to operate or a rate at which a drug or therapeutic fluid is set to be infused. These or other operational parameters of medical device 20 may be stored in memory 36 of controller 30. These operational parameters may be input by the user directly, for example via a touch screen interface on controller 30, or may be input by a clinician. Other operational parameters that may be stored in memory 36 include, for example, the status of power supply 38, the status of any external power supplies, the history of speeds at which the pump actually has operated or the rates at which fluid has actually been delivered, alerts, warnings, and errors in the operation of medical device 20, etc. A number of patient parameters may also be stored by memory 36. Such patient parameters may include, for example, a unique patient identifier, a surgical center, implant/therapy times and dates, a patient's heart rate, temperature, pressure, or any other physiological parameter(s). These patient parameters may be detected by sensors (not illustrated) in or on medical device 20, or may be manually input into controller 30.

Each backup controller 40 may be generally similar or identical to controller 30. For example, each backup controller 40 may include a processor 44, a memory 46, and power supply 48. As shown in the figure, backup controller 40 may also include a user interface, which may be physically part of backup controller 40, such as a touch screen and/or buttons, or may be a separate interface device coupled to backup controller 40. Although two backup controllers 40 are shown with the medical system 10 of FIG. 1, it should be understood that more or fewer backup controllers 40 may be included or used during a course of treatment as part of medical system 10. Further, each backup controller 40 includes an active state and a passive state, with the term "backup" indicating the passive state in which the backup controller 40 is not controlling the medical device 20. Each backup controller 40 may include a pathway for communicating with and/or providing power to medical device 20, although such pathway is not illustrated in FIG. 1 because the backup controllers 40 are in the passive state and are not controlling medical device 20. In addition, each backup controller 40 may include a communication pathway 41 for communicating with active controller 30. Pathway 41 may be a wired or wireless connection.

During operation of active controller 30, memory 36 of active controller may update for any one of a number of reasons. For example, as noted above, the patient or a clinician may update a desired operational parameter stored within memory 36 to change the therapy of medical device 20. Operational parameters may be updated without user intervention, for example upon detecting a fault within power supply 38 or an external power supply, such as a battery pack. Any historical information stored within memory 36 may be automatically updated periodically, including patient parameters and operational parameters. For example, it may be desirable to keep track of a patient's heart rate, hematocrit, blood flow and/or temperature over time so that a clinician or other user may review patient data. This may be beneficial to diagnose changes or potential problems with medical device system 10 or otherwise to try to optimize the operation of the system 10.

Active controller 30 may continually communicate with the backup controllers 40, for example upon a change in information stored in memory 36 and/or at regular intervals, via communication pathway 41, to update the memories 46 such that the information stored in the memories 46 of the backup controllers 40 matches the information stored in the memory 36 of the active controller. As noted above, communication pathways 41 may be wired or wireless, such as via radio-frequency communication. However, it should be understood that other types of free-space communication may be suitable, such as optical communication. Preferably, if communication pathways 41 are wireless, the active controller 30 and backup controllers 40 contain a unique code, identifier, or other recognition capability so that active controller 30 only updates information stored within the memory of backup controllers 40, minimizing the risk that otherwise identical backup controllers in a medical device system of another patient are updated by active controller 30 inadvertently. Communication pathways 41 may alternately be wired. It should also be understood that communication pathway 41 need not be a direct pathway from backup controller 40 to active controller 30, and may include an intermediary such as a network.

In the case of a controller failure, active controller 30 may not be able to control medical device 20 properly, or at all. Any one of the backup controllers 40 may be connected to medical device 20 upon failure of active controller 30. For example, if pathway 32 is a physical connection, pathway 32 may be unplugged from active controller 30 and plugged into a backup controller 40. Alternately, if pathway 32 is wireless, backup controller 40 may be manually put into communication with medical device 20, for example by accessing a settings menu of backup controller 40 or via wireless instructions from another device to assign the backup controller 40 the active status. Once the backup controller 40 is put into communication with medical device, the backup controller 40 switches to the active state.

Similarly, the previous active controller 30 switches to the passive state once communication pathway 32 is disconnected. Although the switching of an active controller 30 to a backup controller 40 would normally be prompted by failure of an active controller 30, the patient or other user may switch between an active controller 30 and a backup controller 40 for another reason.

Once backup controller 40 is connected to medical device 20, the controller takes over operation of medical device 20 and performs all the functions previously described for controller 30. For example, after backup controller 40 is put into the active state, it controls the operation of medical device 20 and updates any remaining backup controllers still capable of being updated. This may include the previous active controller, as the previous active controller may still be functioning properly or at least enough for information stored in memory 36 in that failed or removed controller to be updated.

Figure 2:
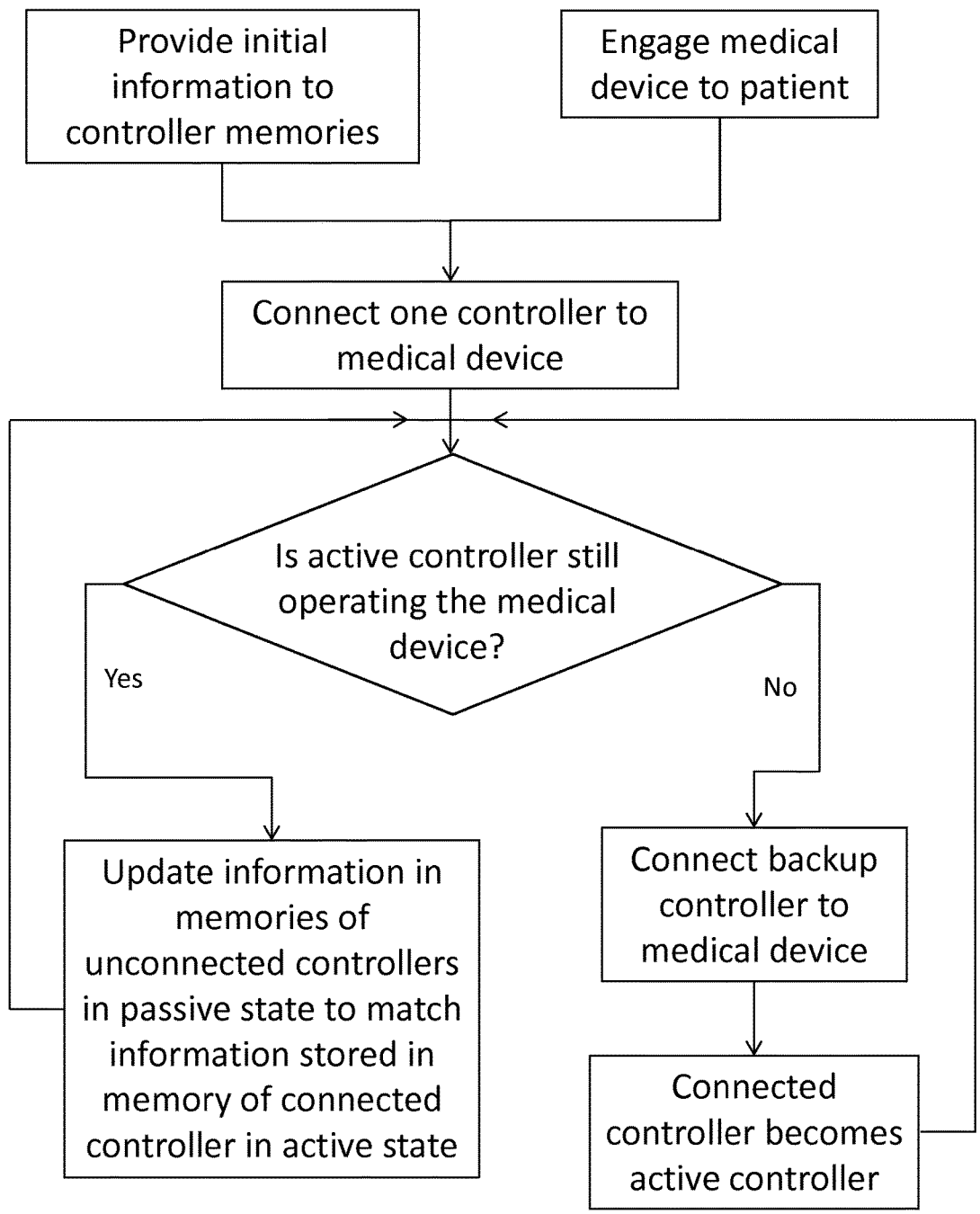
FIG. 2 is a flowchart of a method according to an embodiment of the disclosure.

An exemplary method of operation according to an aspect of the disclosure is illustrated in a flow chart in FIG. 2. The initial steps include engaging medical device 20 to the patient. This may entail, for example, implanting a VAD into a patient or connecting a drug pump to the patient. Before, after, or simultaneously to engaging medical device 20 to the patient, initial information is provided to the memory of at least one controller. Preferably, a first controller is uploaded with all the information needed to operate medical device 20. Secondary controllers may also be provided with the same set of information, but should contain at least enough information to allow updating memory within the secondary controllers by the first controller. The first controller is connected to medical device 20, and is switched to the active state, illustrated as controller 30 in FIG. 1. The remaining controllers are in the passive state, as they are not operating the medical device 20 at this time, illustrated as backup controllers 40 in FIG. 1. The controllers may initially include, for example, an encrypted set of unique patient information and device identification and time stamp, forming a kernel of entire memory, which may initially set each controller as in the active or passive state.

Operation of the medical device 20 by active controller 30 continues for as long as possible or desired. As long as active controller 30 is in the active state and is controlling medical device 20, it will periodically connect with the backup controllers 40 to update the information in memories 46 of the backup controller 40 to match the information stored in memory 36 of the active controller 30. As noted above, this updating may occur at regular intervals or otherwise upon a change in information stored in the memory 36 of active controller 30. For example, active controller 30 may be programmed to update the information stored in memories 46 of the backup controllers 40 every 5 minutes, 10 minutes, minutes, 30 minutes, hour, day, etc. It should be understood that these intervals are merely exemplary, and any desired interval may be used, for examples ones based on risk analysis. In addition or in the alternative, anytime information stored in memory 36 of controller 30 is updated, controller 30 may in turn update the information stored in memory 46 of the backup controllers 40. The type of information update triggering such a "push" style update may be any desired information. However, it may be particularly useful to engage in such a "push" update only when particularly important information is updated in memory 36. For example, for a VAD, anytime the hematocrit or set speed of the motor of the pump is updated, that update may trigger controller 30 to update the memories 46 of backup controllers 40. Similarly, for a drug infusion system, anytime the basal rate of drug delivery is updated, controller 30 may be triggered to cause an update in the memories 46 of the passive controllers 40. It should be understood that the references herein to "the information" includes all information or only some information stored in memory, including specific sets or subsets of information. As used herein, the term "continual" in reference to updating or communicating means "push"-style communication and/or periodic communication, including at regular intervals.

If the active controller 30 stops operating the medical device 20 for any reason, for example due to failure or intentional disconnection, the patient should connect a backup controller 40 to the medical device 20. The newly connected controller effectively becomes active controller 30, and operation of the medical device 20 continues.

As should be clear from the above description, a number of benefits arise from the medical systems disclosed herein. For example, in the case of failure of controller 30, the patient is able to connect a backup controller 40 to the medical device 20 immediately and have little to no interruption in the treatment being provided by the medical device 20. The control provided by the newly connected backup controller may be identical to the control provided by the previous controller, regardless of whether instructions in the previous active controller have been updated. Similarly, historical information stored in the previous controller is not lost, but is rather already contained on the newly connected controller because of the continual memory updates. In other systems, a backup controller may have outdated information stored in memory, and upon connection of a backup controller to the medical device, operation of the medical device under the new controller may be different than operation of the medical device under the old controller. Even if no control information has changed between the old and new controller, any historical operation or patient parameter stored on the old controller is not lost.

Backup controllers 40 are continually updated by the active controller 30 as the active controller 30 operates the medical device 20, without the need to store or transfer any sets of backup data to the medical device 20 for safekeeping. The continual updating is also performed without any intervention by the user or a clinician, as the updates are automatic. Additionally, with the medical systems disclosed herein, visits to the doctor and/or clinician may be reduced or expedited. For example, in other medical systems, if a patient visited his clinician to update operational parameters of an active controller, he would need to bring all of his backup controllers so that the clinician could update the entire set of controllers in one visit, generally one at a time. Patients may forget to bring any or all backup controllers, resulting in all of the backup controllers not being updated and thus having outdated information. Even if the patient brought all backup controllers, the time to update the entire set of controllers may be appreciably longer than the time required to update only the active controller. Medical device system 10 may eliminate both of these problems since, as long as active controller 30 is updated, the backup controllers 40 will be updated in the normal course of operation.

Figure 3:
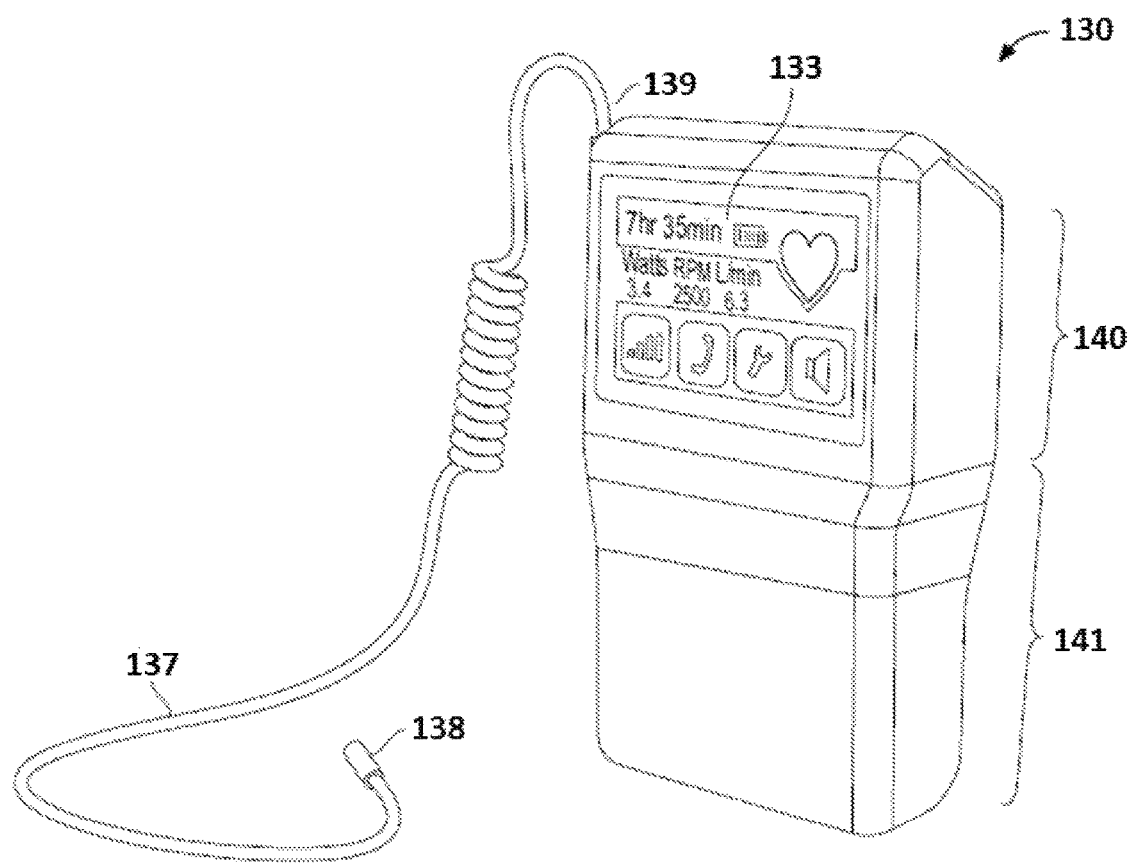
FIG. 3 is a perspective view of a medical device controller/monitor according to an aspect of the disclosure.
Figure 4:
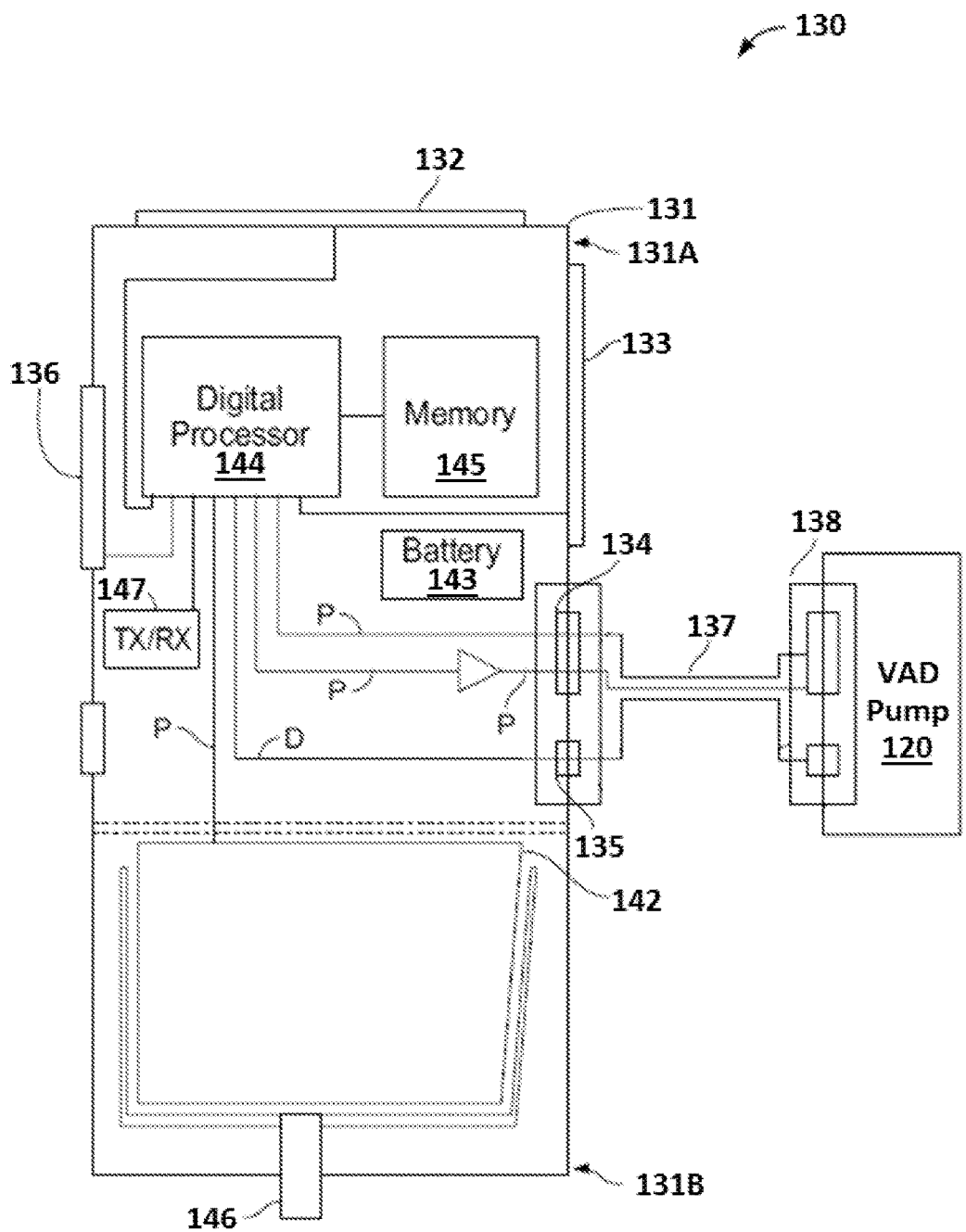
FIG. 4 is a diagrammatic view of the components of the controller of FIG. 3 coupled to a medical device.

An exemplary controller 130 for use with a VAD 120 in a medical device system is described with reference to FIGS. 3-4. As shown in the figures, controller 130 includes a housing 131 extending between a top end 131A and a bottom end 131B. A first display 132 is disposed on the outer surface of top end 131A and a second display 133 on a back portion of housing 131. The displays 132, 133 may act as user interfaces. The housing 131 may also include a power port 134, a data port 135, and an input device 136. An elongated flexible electrical cable 137 may extend from the housing 131. A medical device connector assembly 138 may be disposed at one end of cable 137 and a controller connector assembly 139 may be disposed at the other end. When the controller connector assembly 139 is connected to the controller 130, and the medical device connector assembly 138 is connected to the pump of a VAD 120, pump drive signals can pass to VAD 120 from the power port 134 and data can pass between VAD 120 and the data transfer port 135.

The housing may be split into two opposed components: upper housing portion 140 and lower housing portion 141. Lower housing 141 may include in its interior a battery 142, which may be replaceable. A secondary, or backup, battery 143 may be disposed within the interior of upper housing 140, and may be coupled to the various elements in controller 130. The upper housing 140 may also contain a digital signal processor 144 and an associated memory 145.

An electrical power conductor assembly P may be disposed within controller 130. That electrical power conductor assembly P couples electrical power from a power supply (whether it be from a battery 142 or from an external source by way of power jack 146 or from secondary battery 143), and provides electrical power to all elements in the controller 130. In addition, the electrical power conductor assembly P provides a power drive signal line from the digital processor 144, by way of a power amplifier, to the electrical power output port 134, where that power drive signal can be coupled via cable 137 to the motor (not shown) of the pump of VAD 120. A data conductor assembly D may also be disposed within controller 130. The data conductor assembly D may provide analog data representative of the current state of the motor of the pump of VAD 120, received via cable 137, to the digital processor 144.

The input device 136 in some forms includes a keyboard, and in other forms includes a connector, and in still other forms, includes both. Through the input device 136, a user of, or administrator for, the controller 130 can activate or deactivate the system, or can add, modify or delete any information associated with the operation of the system, for example by modifying the information stored in memory 145.

The memory 145 may store program information, for example, for controlling the operation of one of a number of (same or different model) implantable blood pumps which might be connected to, and driven by, the controller 130. The digital processor 144 may be adapted to run and control the overall system as well as a pump of a VAD 120 attached thereto via cable 137. Displays 132 and 133 are driven by the processor 144 to selectively display information which is generally useful to an administrator of a VAD 120, such as a nurse or physician.

In operation, controller 130, when deployed, is coupled by way of cable 137 to a pump of a VAD 120. Controller 130 adaptively generates and applies by way of the power port 134, control signals (e.g. pump drive signals) for driving the pump of the VAD 120. Controller 130 effectively monitors in real time the operation of the pump of VAD 120, based on the impedance of the windings of the pump's motor, and generates appropriate time-based pump drive signals for application to those windings, to achieve the performance defined by the pump's program stored in memory 145.

Also included within the housing 130 is a wireless transmitter/receiver TX/RX 146. Transmitter/receiver 146 is coupled to the digital processor 144 and is adapted to selectively transmit and receive data. By way of example, the transmitted data may be representative of indicia of operation of the VAD 120, to a main processor. The information can be selected to include data representative of broad aspects of the operation of the connected VAD 120, such as pump activity, fault conditions, warning/alarm conditions and other data necessary for comprehensive logs for the pump. The received data, by way of example, may be program or control instructions, or modifications, for use in the control of VAD 120. In other embodiments, the data transfer may be accomplished via a wired line. In addition to providing for communication with a clinician computer system, transmitter/receiver TX/RX 146 may transmit and receive data with other backup controllers to perform the updating described above in connection with FIGS. 1-2. Similarly, if controller 130 becomes disconnected from VAD 120 and a backup controller is then connected to VAD 120, transmitter/receiver TX/RX 146 may receive data from the newly connected controller to update information stored in memory 145 as controller 130 is now a backup controller. Other controllers for use with a VAD are described in greater detail in U.S. Patent Publication No. 2014/0194985, the disclosure of which is hereby incorporated by reference herein.

Although the invention herein has been described with reference to particular embodiments, it is to be understood that these embodiments are merely illustrative of the principles and applications of the present invention. For example, although the medical systems described herein have been described in the context of VADs and transfusion pumps, the concepts apply to other medical systems with medical devices and controllers. It is therefore to be understood that numerous modifications may be made to the illustrative embodiments and that other arrangements may be devised without departing from the spirit and scope of the present invention as defined by the appended claims. Such modifications may include the combination of one or more features of one embodiment of the disclosure with one or more features of another embodiment of the disclosure.

The invention claimed is:

1. A medical device system comprising:
a medical device configured to be carried by a patient; and
a plurality of discrete controllers coupled to and capable of controlling operation of the medical device, each controller having an active state in which the controller is in communication with the medical device and is controlling operation of the medical device, a passive state in which the controller is not controlling operation of the medical device, and a memory for storing information, the device and the plurality of discrete controllers being constructed and arranged so that at any given time only one of the plurality of discrete controllers will be in the active state and a remainder of the plurality of discrete controllers will be in the passive state,
each of the plurality of discrete controllers in the active state being configured to automatically update with information associated with the medical device and continually communicate with the remainder of plurality of discrete controllers in the passive state to update at least some of the information stored in the memories of the remainder of controllers in the passive state to match the information in the memory of the controller in the active state, without using the medical device as an intermediary in such updating; each of the plurality of discrete controllers including a unique identifier enabling communication with another one of the plurality of discrete controllers.

2. The system of claim 1, wherein the information stored in the memories of the plurality of discrete controllers relates to an operational parameter of the medical device.

3. The system of claim 2, wherein the medical device is a ventricular assist device.

4. The system of claim 3, wherein the operational parameter is selected from the group consisting of blood flow and a speed of a pump of the ventricular assist device.

5. The system of claim 1, wherein each of the plurality of discrete controllers is substantially identical to one another.

6. The system of claim 1, wherein the information stored in the memories of the plurality of discrete controllers relates to one or more patient parameters sensed by the medical device.

7. The system of claim 6, wherein the one or more patient parameters includes at least one parameter selected from the group consisting of heart rate, hematocrit, temperature, and pressure.

8. The system of claim 1, wherein each of the plurality of discrete controllers is configured to be physically connected to the medical device when in the active state.

9. The system of claim 8, wherein, upon being physically connected to the medical device, the connected controller transitions from the passive state to the active state.

10. The system of claim 1, wherein each of the plurality of discrete controllers in the active state is configured to automatically update at least some of the information stored in the memory of the remainder of the plurality of discrete controllers in the passive state at regular intervals.

11. The system of claim 1, wherein the controller in the active state is configured to continually communicate with the remainder of the plurality of discrete controllers in the passive state without user or clinician intervention.

12. A method of operating a medical device system comprising:
controlling a medical device carried by a patient with one of a plurality of discrete controllers coupled to the medical device, the one of the plurality of discrete controllers being in an active state in which the controller is in communication with the medical device, is controlling operation of the medical device, and receiving automatic updates, a remainder of the plurality of discrete controllers being in a passive state in which the controller is not controlling operation of the medical device;
continually communicating from the controller in the active state to the remainder of the plurality of discrete controllers in the passive state to update at least some information stored in a memory of each of the plurality of discrete controllers in the passive state to match information stored in a memory of the controller in the active state, without using the medical device as an intermediary in such updating, each of the plurality of discrete controllers including a unique identifier enabling communication with another one of the plurality of discrete controllers.

13. The method of claim 12, wherein the information stored in the memories of the plurality of discrete controllers relates to an operational parameter of the medical device.

14. The method of claim 13, wherein the medical device is a ventricular assist device.

15. The method of claim 14, wherein the operational parameter is selected from the group consisting of blood flow and a speed of a pump of the ventricular assist device.

16. The method of claim 12, wherein each of the plurality of discrete controllers is substantially identical to one another.

17. The method of claim 12, wherein the information stored in the memories of the plurality of discrete controllers relates to one or more patient parameters sensed by the medical device.

18. The method of claim 17, wherein the one or more patient parameters includes at least one parameter selected from the group consisting of heart rate, hematocrit, temperature, and pressure.

19. The method of claim 12, wherein each of the plurality of discrete controllers is configured to be physically connected to the medical device when in the active state.

20. The method of claim 19, further comprising the step of physically connecting one of the remainder of the plurality of discrete controllers in the passive state to the medical device and transitioning the connected controller from the passive state to the active state.

21. The method of claim 12, wherein the step of updating information stored in the memory of each of the plurality of discrete controllers in the passive state is performed at regular intervals.

22. The method of claim 12, wherein the step of continually communicating from the controller in the active state to the remainder of the plurality of discrete controllers in the passive state is performed automatically without user or clinician intervention.

* * * * *